United States Patent
Sohn et al.

(10) Patent No.: US 10,765,804 B2
(45) Date of Patent: Sep. 8, 2020

(54) INJECTION DEVICE FOR ENDOSCOPY (71) Applicant: National Cancer Center, Goyang-si, Gyeonggi-do (KR)

(72) Inventors: Dae Kyung Sohn, Goyang-si (KR); Kwang Gi Kim, Seoul (KR); Na Ri Yang, Goyang-si (KR)

(73) Assignee: NATIONAL CANCER CENTER, Gyeonggi-Do (KR)

( * ) Notice: Subject to any disclaimer, the term of this patent is extended or adjusted under 35 U.S.C. 154(b) by 505 days.

(21) Appl. No.: 15/029,575

(22) PCT Filed: Oct. 13, 2014

(86) PCT No.: PCT/KR2014/009562
§ 371 (c)(1),
(2) Date: Apr. 14, 2016

(87) PCT Pub. No.: WO2015/056937
PCT Pub. Date: Apr. 23, 2015

(65) Prior Publication Data
US 2016/0256624 A1  Sep. 8, 2016

(30) Foreign Application Priority Data

Oct. 16, 2013  (KR) .......................... 10-2013-0123509
Oct. 10, 2014  (KR) .......................... 10-2014-0136540

(51) Int. Cl.
*A61B 17/29* (2006.01)
*A61M 5/158* (2006.01)
(Continued)

(52) U.S. Cl.
CPC ............. *A61M 5/158* (2013.01); *A61B 17/29* (2013.01); *A61B 17/3478* (2013.01);
(Continued)

(58) Field of Classification Search
CPC .................... A61M 5/158; A61M 5/00; A61M 2005/1588; A61B 17/29; A61B 17/3478;
(Continued)

(56) References Cited

U.S. PATENT DOCUMENTS 4,222,380 A * 9/1980 Terayama ............. A61M 5/425
600/104
5,919,202 A    7/1999 Yoon
(Continued)

FOREIGN PATENT DOCUMENTS

CN    101227864 A    7/2008
CN    102204843 A    10/2011
(Continued)

OTHER PUBLICATIONS

Supplementary European Search Report and Written Opinion received for EP Patent Application No. 14854246.7, dated May 10, 2017, 9 pages.
(Continued)

*Primary Examiner* — Eun Hwa Kim
*Assistant Examiner* — Catherine Premraj
(74) *Attorney, Agent, or Firm* — Womble Bond Dickinson (US) LLP (57) ABSTRACT

The present invention relates to an injection device for endoscopy, and provides: a feature of inserting a needle for endoscopy into a tissue, in a state of holding a body tissue, which is a region to receive an injection, and then injecting an injection solution thereinto; and a feature enabling stanching of the bleeding region if bleeding occurs. That is, tissue is held by holding forceps and a needle is inserted thereinto, corresponding to a series of operations from a state in which the needle is accommodated between the holding forceps for holding the tissue, and then an injection solution is injected into the tissue through the needle. In
(Continued)

addition, a bleeding region is stanched by the heat transferred to the holding forceps without using a separate hemostat if bleeding occurs during the operation. According to the present invention, the precise position of an injection target region can be confirmed, and thus the generation of a tissue perforation due to a needle can be prevented, and bleeding can be immediately stanched without using a separate tool if bleeding occurs.

7 Claims, 6 Drawing Sheets (51) Int. Cl.
  *A61B 17/34* (2006.01)
  *A61B 18/14* (2006.01)
  *A61B 18/08* (2006.01)
  *A61B 17/00* (2006.01)
  *A61B 18/00* (2006.01)
  *A61B 90/00* (2016.01)

(52) U.S. Cl.
  CPC ........ *A61B 18/085* (2013.01); *A61B 18/1445* (2013.01); *A61B 17/2909* (2013.01); *A61B 2017/00269* (2013.01); *A61B 2017/2926* (2013.01); *A61B 2018/00029* (2013.01); *A61B 2090/067* (2016.02); *A61B 2218/002* (2013.01); *A61B 2560/0266* (2013.01); *A61M 2005/1588* (2013.01)

(58) Field of Classification Search
  CPC ............ A61B 17/2909; A61B 2010/45; A61B 18/1445; A61B 18/085; A61B 2090/067; A61B 2017/00269; A61B 2017/2926; A61B 2018/00029; A61B 2018/002; A61B 2560/0266
  See application file for complete search history.

(56) References Cited

U.S. PATENT DOCUMENTS

| | | |
|---|---|---|
| 5,931,810 A | 8/1999 | Grabek |
| 6,066,102 A | 5/2000 | Townsend et al. |
| 6,099,550 A * | 8/2000 | Yoon ...................... A61B 10/06 606/205 |
| 2003/0018249 A1 | 1/2003 | Sferco |
| 2005/0049520 A1* | 3/2005 | Nakao .................... A61B 10/06 600/562 |
| 2009/0125026 A1* | 5/2009 | Rioux ................ A61B 18/1442 606/45 |
| 2009/0261804 A1* | 10/2009 | McKenna .......... A61B 18/1442 324/71.1 |
| 2010/0049139 A1* | 2/2010 | Kiyono ................. A61M 5/158 604/180 |
| 2011/0054469 A1* | 3/2011 | Kappus .............. A61B 18/1445 606/46 |
| 2011/0230910 A1* | 9/2011 | Stopek ................... A61B 17/29 606/205 |
| 2012/0226300 A1 | 9/2012 | Mitelberg et al. |

FOREIGN PATENT DOCUMENTS

| | | |
|---|---|---|
| CN | 102357042 A | 2/2012 |
| EP | 1525852 A1 | 4/2005 |
| JP | 05-184535 A | 7/1993 |
| JP | 08-117232 A | 5/1996 |
| JP | 2003-225242 A | 8/2003 |
| JP | 2005-058344 A | 3/2005 |
| KR | 10-2012-0055874 A | 6/2012 |
| WO | 2012/086215 A1 | 6/2012 |

OTHER PUBLICATIONS

Office Action received for Chinese Patent Application No. 201480057167.X, dated May 30, 2018, 23 pages (13 pages of English Translation and 10 pages of Office Action).

International Search Report and Written Opinion received for PCT Patent Application No. PCT/KR2014/009562, dated Dec. 24, 2014, 18 pages (10 pages of English Translation and 8 pages of Original Document).

International Preliminary Report on Patentability received for PCT Patent Application No. PCT/KR20141009562, dated Apr. 28, 2016, 16 pages (10 pages of English Translation and 6 pages of Original Document).

* cited by examiner

INJECTION DEVICE FOR ENDOSCOPY

TECHNICAL FIELD

The present disclosure relates to an injection apparatus, and more particularly an endoscopic injection apparatus for multiple purpose which stably inserts a needle into a tissue for endoscopy, in a state of holding a body tissue, which is a region to receive an injection and enables stanching of the bleeding region if bleeding occurs.

BACKGROUND

As the living standard improved with industrial development, interests in health increased and thereby, field of medicine and medical appliances are also developing.

The field of therapeutic endoscopy using endoscope is especially acknowledged as an important field in medical treatment of digestive system among the medical fields. That is, in a case of gastric cancer and colorectal cancer, the treatment relied on surgical operation in the past. However, due to the advent of endoscope, the treatment rate is increasing through clinically implementing diagnosis and treatment at the same time.

An endoscopic injection apparatus is one of medical appliances used in such field of endoscopy and it is used as a device to inject medicine in a patient's body for endoscopy operation.

As a prior injection apparatus for endoscopy, 'injector for endoscopic treatment' is disclosed in Korean patent publication 10-2012-0055874 (hereinafter, referred to as 'R1')

Referring to R1, the injector for endoscopic treatment mainly comprises a treatment unit which controls operation required to inject medicine in the body tissue, a needle unit formed with a needle which is inserted in the treatment unit and injects medicine in the body tissue and, a medicine injection unit which includes the medicine which is injected in the tissue when it is combined with an end unit of the needle unit. Further, the operation thereof injects the medicine stored in the medicine injection unit in the body by operating the treatment unit in a state of inserting the needle in the injection target area.

However, the following problems may be generated in case of injecting medicine using an injector for endoscopic treatment according to R1.

That is, the injector for endoscopic treatment according to R1 only comprises a needle in one end.

In the above case, the one end of the needle may be inserted in a tissue by directly pushing in the tissue when it is contacting with the injection target tissue area. However, the needle may not be inserted in the accurate area where it should be inserted due to subtle movement of the tissue. Thus, the operator may generate an unwanted wound on the tissue since, the operator should hold the injector for endoscopic treatment again and, insert the needle in the accurate part again.

Figure 1:
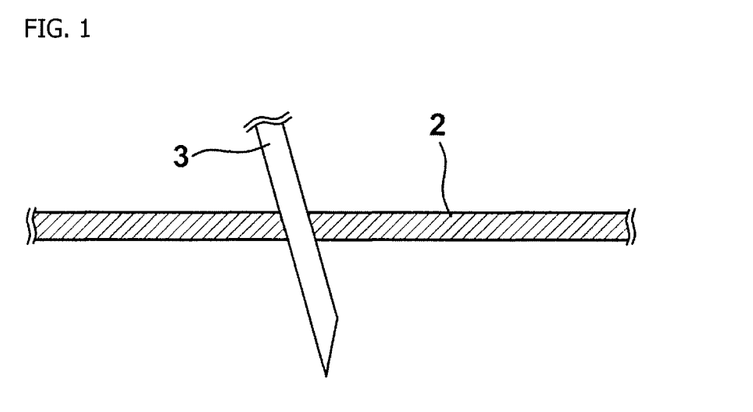
FIG. 1 is an exemplary diagram illustrating when using a needle on a colon tissue and etc. according to a related art.

Further, when injecting an injection solution in the organ tissue such as a colon, the injection solution should only be inserted in the colon tissue. However, since the thickness of the colon is substantially thin which is within 3-5 mm, the medicine passes right through the colon thereby, causing perforation in the colon. That is, when inserting the needle 3 in the colon as shown in FIG. 1, the needle 3 often directly passes through the colon thickness 2.

Due to above problems, in a related art, other problems such as the injection solution can be leaked to other areas and not the injection target area which can lead to a severe problem resulting from an operation side effect.

Further, bleeding often can be generated when the needle penetrates the tissue. In this case, a separate hemostat which a separate electric device can be connected is used to stanch the bleeding region. When the hemostat is used, the operation can be uncomfortable and cumbersome since the injector and hemostat should be used in turns.

TECHNICAL SOLUTIONS

The present description aims to solve the above problem by providing an endoscopic injection apparatus to insert a needle for endoscopy into a tissue, in a state of holding a body tissue, which is a region to receive an injection, and then injects an injection solution thereinto.

The present description aims to provide the endoscopic injection apparatus which enables immediate stanching of the bleeding region without using a separate hemostat if bleeding occurs during the operation.

That is, the present application provides multiple functions that an endoscopic injection apparatus injects an injection solution in the accurate injection targeted area and in case of bleeding, a bleeding region is stanched without the use of separate hemostat.

SUMMARY OF INVENTION

Solution to Problem

In an effort to accomplish the afore-mentioned aim, the present description discloses an endoscopic injection apparatus including a needle which injects injection solution; a pair of holding forceps which surrounds the needle; and an operation unit which holds the injection targeted area using the holding forceps and injects the injection solution when the needle is inserted in the tissue.

The operation unit includes a body with a needle operation button on one end; an injection hole for the injection solution which is formed on the body; and a forceps operation unit which surrounds the exterior body and configured to operate the holding forceps according to a sliding movement.

The operation unit further includes a power button configured to operates a power supply which is applied from the power supply unit to the holding forceps.

The power button operates only when the needle operation button is not operating.

Further, a predetermined length of shaft which is connected with another end of the body and; wherein the holding forceps combines with an inner one end of the shaft and a part of the shaft is protruded outside the shaft and the holding forceps is hinged and combined with a fixing piece with an incision unit formed in the middle thereof.

Further, a guide groove is formed on the holding surface of the holding forceps for the movement of the needle, and the holding surface is formed in a concavo-convex shape.

A conductor configured to generate heat by the power supply which is applied according to the operation of the power button and is formed on the end of the holding surface.

A sensor configured to sense a spread angle of the holding forceps, and a notification unit configured to display a sensing result of the sensor and, the needle operation button is configured not to operate when the holding forceps are spread.

While the needle operation button operates, the needle moves as much as a predetermined distance and it is inserted in the tissue.

The body further includes an elastic member for a forward and backward movement of the forceps operation unit.

A fixing member configured to fix the needle which is formed with a predetermined length and diameter as to be inserted and installed in the shaft.

Effects of Invention

An endoscopic injection apparatus which provides such features according to the present description inserts the needle in the tissue, in a state of stably holding an injection targeted tissue area with a holding forceps. Hereinafter, the injection solution is inserted in the tissue.

Accordingly, the injection solution can be injected after confirming the accurate position of the area to be injected. Thereby, wounds generated by a needle can be prevented since unnecessary operation of extracting and inserting the needle by selecting the wrong injection targeted area, can be avoided.

Further, generation of perforation in the colon tissue can be minimized since the needle is inserted in a state of holding the injection targeted area with a holding forceps.

Further, although bleeding occurs due to generation of perforation in the injection targeted area, a further stable operation is possible since stanching of the bleeding area is possible only with the endoscopic injection apparatus.

Further, the all operation can be easily controlled through one operation unit.

METHOD FOR CARRYING OUT THE INVENTION

Certain exemplary embodiments of the present inventive concept will now be described in greater detail with reference to the accompanying drawings. In the following description, same drawing reference numerals are used for the same elements even in different drawings. The matters defined in the description, such as detailed construction and elements, are provided to assist in a comprehensive understanding of the present inventive concept. Accordingly, it is apparent that the exemplary embodiments of the present inventive concept can be carried out without those specifically defined matters. Also, well-known functions or constructions are not described in detail since they would obscure the invention with unnecessary detail. Hereinafter, an embodiment of the present disclosure is described in detail referring to the attached drawings.

Figure 2A:
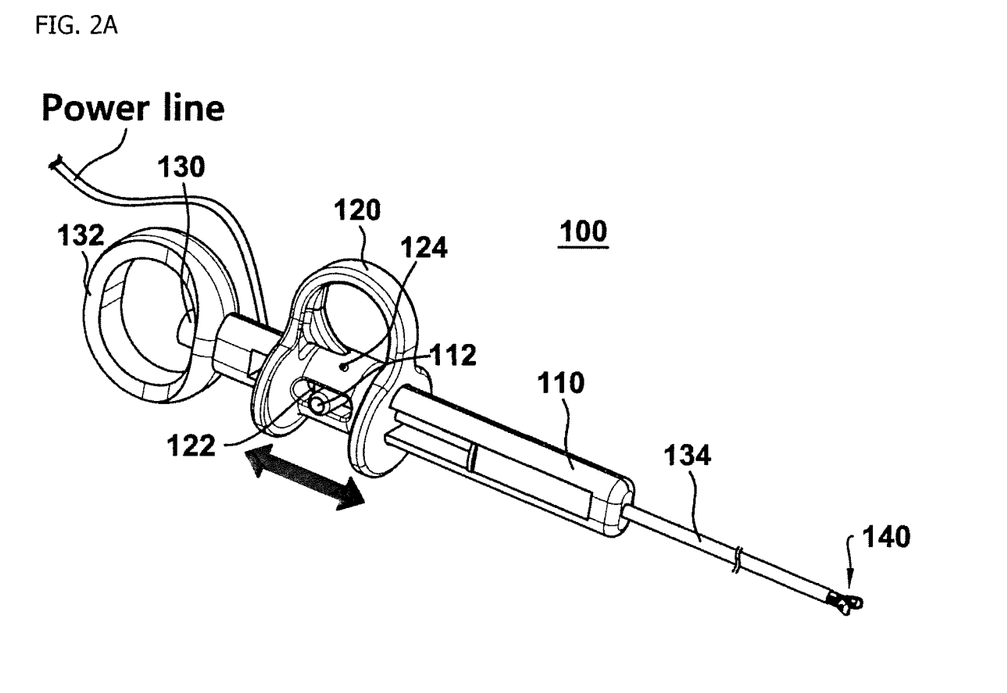
FIG. 2A and FIG. 2B is a perspective view illustrating an endoscopic injection apparatus according to an exemplary embodiment of the present description.
Figure 2B:
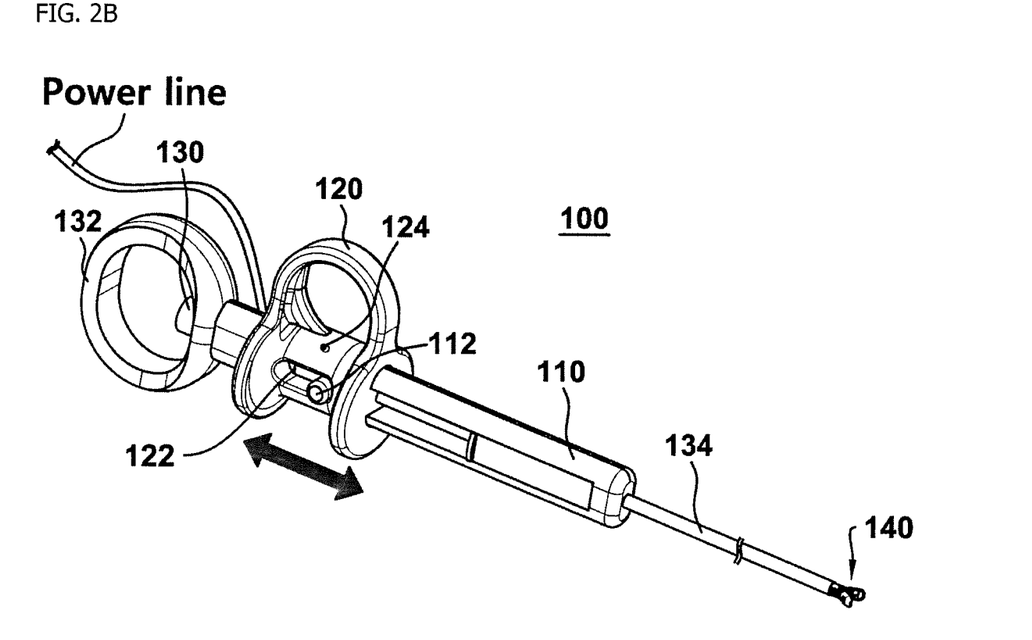
Figure 3:
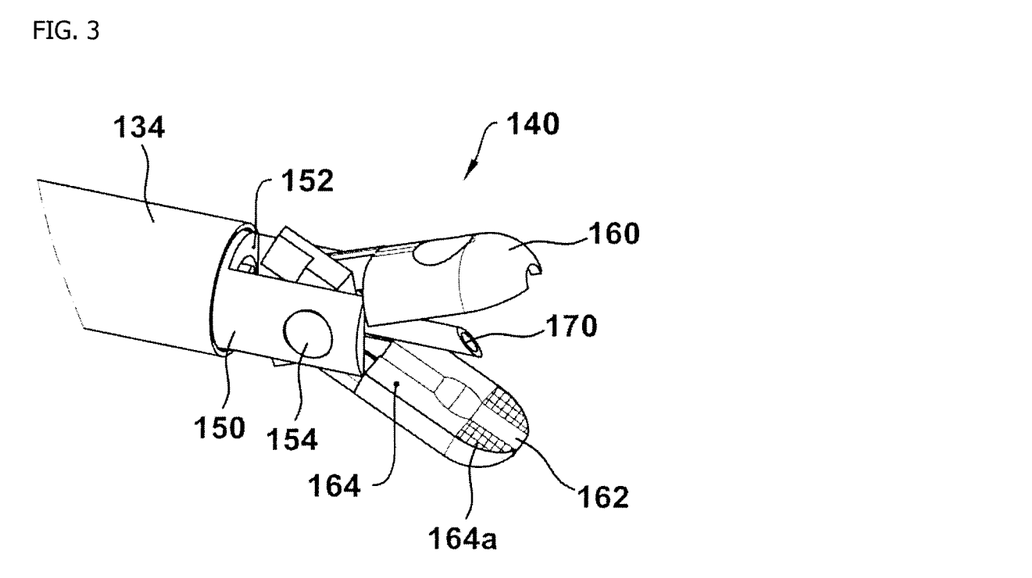
FIG. 3 is an enlarged view of a part of the features of FIG. 1.

FIG. 2A and FIG. 2B is a perspective view illustrating an endoscopic injection apparatus according to an exemplary embodiment of the present description and, FIG. 3 is an enlarged view of a part of the features of FIG. 2.

Referring to FIG. 2 and FIG. 3, the frame and mold of the endoscopic injection apparatus is formed by a body 110. The body 110 is a form which is overall long transversely as shown in the diagram. The length may be enough to easily inject an injection solution in the injection targeted area using the endoscopic injection apparatus 100.

The forceps operation unit 120 is installed in an outer circumference surface of the body 110. The forceps operation unit 120 slides by the user according to the outer circumference surface of the body 110. Due to the sliding, the holding forceps 160 which is mentioned hereinafter is spread or closed. That is, when the forceps operation unit 120 is formed as shown in FIG. 2A, the holding forceps 160 is spread and when the forceps operation unit 120 slides as shown in FIG. 2B, the holding forceps 160 is closed. Further, a notification unit 122 is formed on the forceps operation unit 120. The notification unit 122 is an incision of a part of a forceps operation unit 120, and herein, an injection solution hole 112 formed on the body 110 is protruded. The injection solution hole 112 is configured to inject an injection solution thereby, a syringe is installed in the injection solution hole 112. Further, a power button 124 is installed in the forceps operation unit 120. The power button 124 is configured to control heat applied to the holding forceps 160 through a wire to stanch the bleeding area using the holding forceps 160. Thus, the holding forceps 160 may be formed with a material which can stanch the bleeding area with the applied heat which will be illustrated hereinafter.

A needle operation button 130 is configured in one surface of the body 110 to move a needle 170. When the needle operation button 130 is operated, the needle 170 moves as much as a predetermined distance and inserted in a tissue during the operation. Further, a boundary 132 is formed in a circumference of the needle operation button 130. The boundary 132 is to easily operate the needle operation button 130 when an operator's finger is inside thereof. If there is no boundary 132, the finger is always apart from the needle operation button 130 thereby causing discomfort since the finger may be on the side of the needle operation button 130.

Meanwhile, the needle operation button 130 can be operated only when the holding forceps 160 is closed by the forceps operation unit 120. That is, when operating the needle operation button 130 in a state of the holding forceps 160 is spread, it may generate perforation as the needle directly passes through a colon tissue since the tissue is not held. Accordingly, the present description provides the needle operation button 130 configured to operate only when an angle of the holding forceps 160 is within the predetermined angle. According to an exemplary embodiment of the present description, the holding forceps 160 may be operated only when the angle is approximately within 45°. This can be deemed as a state which the holding forceps 160 is holding the injection targeted area. Accordingly, a sensor configured to sense a spread angle of the holding forceps 160 may be further included. The sensor is not shown in the drawing however, it can be installed in the hinge axis 154 of the holding forceps 160. Further, according to the spread angle of the holding forceps 160 as a result of a sensing result of the sensor, a notification unit such as a lamp may be further included for the operator to signal to reoperate the needle operation button 130. The notification unit may be formed on the body 110. In other words, when the lamp is on, the holding forceps 160 is currently not holding a tissue hence, the needle operation button 130 cannot be operated. Thus, the lamp signals to operate the forceps operation unit 120 again and hold the tissue again.

A shaft 132 which is hollow inside has a predetermined length and connected to another end of the body 110. Although not shown, a first wire configured for an operation of the holding forceps 160 and a second wire configured to control heat which is applied for stanching of a bleeding area using the holding forceps 160 is provided in the shaft 134. That is, the first wire connects the holding operation unit 120 and the holding forceps 160 and the second wire connects the power button 124 and the holding forceps 160. Further, the needle 170 configured to move by the needle operation button 130 is also installed.

A holding unit 140 is formed at an end of one side of the shaft 134. The holding unit 140 includes a holding fixing piece 150, a pair of holding forceps 160 and a needle 170. Hereinafter, illustrates the features thereof.

First, the holding fixing piece 150 is combined with an inner side of one end and a part thereof protrudes outside the shaft 134 and the middle is formed with an incision unit 152. The pair of holding forceps 160 is installed in the incision unit 152 and the holding forceps 160 intersects while driving in reference to the hinge axis 154.

The holding forceps 160 which hinges and combines with the forceps fixing piece 150 may be a form that can receive a needle 170. That is, the needle 170 may be possible to move in a state of the holding forceps 160 holding a tissue. For this, a guide groove 162 which is a moving route of the needle is formed in the holding forceps 160. The guide groove 162 refers to a part of the holding surface 164 with a concave shape. Meanwhile, the holding surface 164 of the holding forceps 160 may be any shape which can hold a part of a tissue. For example, the holding surface 164 may be formed in a flat shape or a sawtooth shape which can improve the holding function to grab the tissue of the injection targeted area. Further, the holding surface 164 is also configured to stanch a bleeding area and for this, a part of the holding surface 164 end may be formed with a conductive material 164. Such stanching is only possible when the needle 170 does not operate. That is, when the needle operation button 130 operates and the needle 170 further protrudes than the holding forceps 160, the power button 124 may not operate.

The needle 170 is provided in the holding forceps 160. The needle 170 is normally positioned in the holding forceps 160 and when the needle operation button 130 operates, it slides forward and is further protruded than the holding forceps 160. Such needle 170 may slide along the guide groove 162 even when the holding forceps 160 is completely closed as afore-mentioned.

Figure 4A:
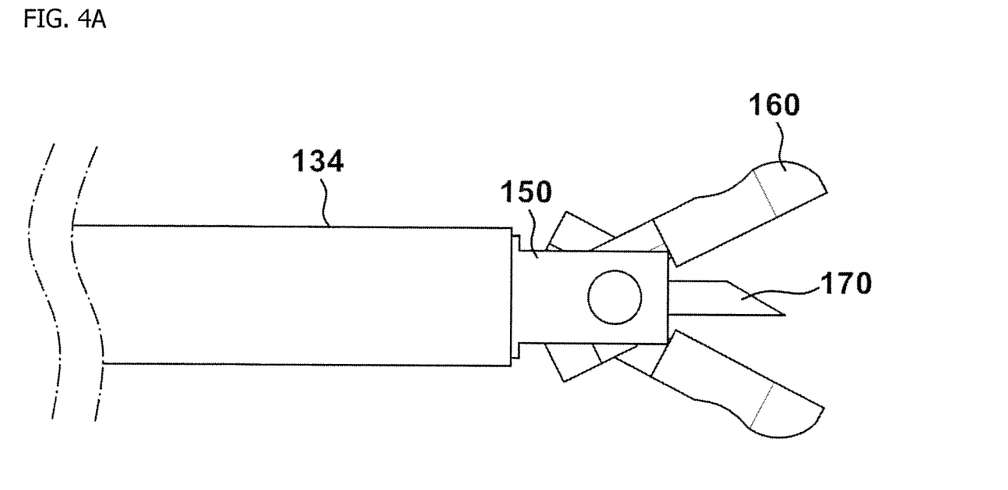
FIG. 4A and FIG. 4B are side view and top plan view illustrating a part of exemplary features of the operation state of an endoscopic injection apparatus of FIG. 1.
Figure 4B:
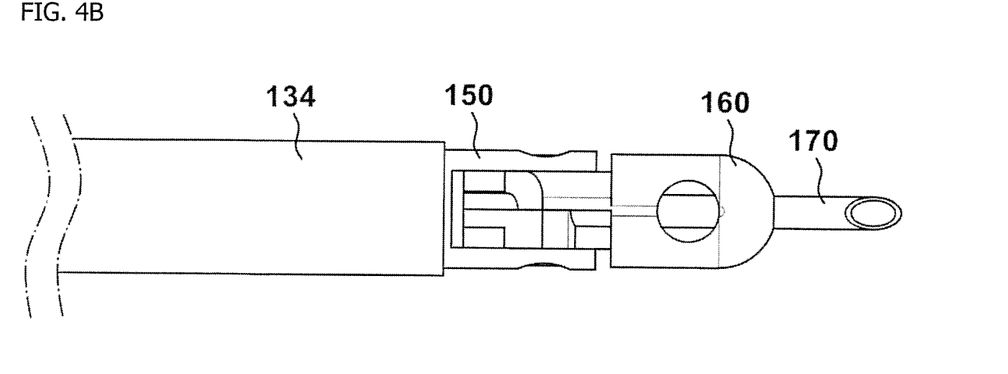

FIG. 4A and FIG. 4B are a side view and a top plan view illustrating a part of exemplary features of the operation state of an endoscopic injection apparatus of FIG. 2.

FIG. 4A illustrates the holding forceps 160 of the endoscopic injection apparatus 100 spread. Herein, the needle 170 accommodated by the holding forceps 160 is almost completely accommodated in the holding forceps 160. It is a state which the injection solution may not be injected. On the other hand, FIG. 4B illustrates that the holding forceps 160 of the endoscopic injection apparatus 100 is closed and herein, the needle 170 further protrudes than the holding forceps 160. Accordingly, in this case, it is deemed that the needle is inserted in a body tissue in a state the holding forceps is holding the tissue.

Figure 5A:
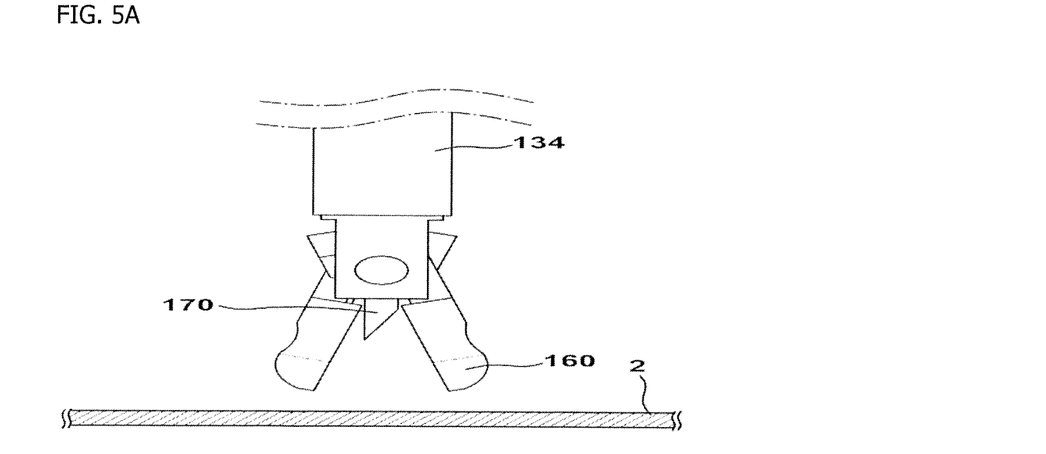
FIG. 5A to FIG. 5C is an operation state view of an endoscopic injection apparatus of FIG. 1.
Figure 5B:
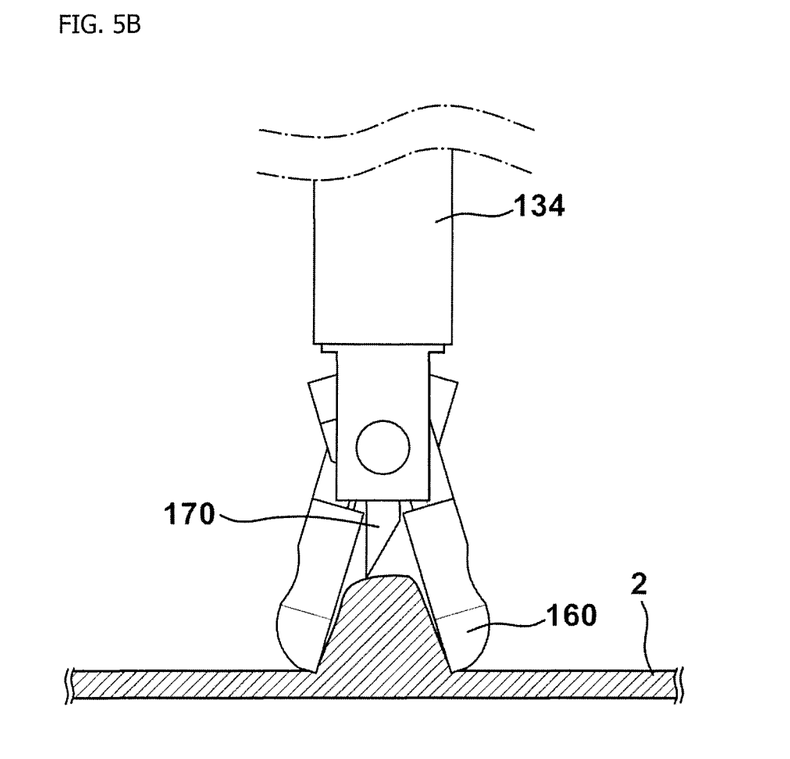
Figure 5C:
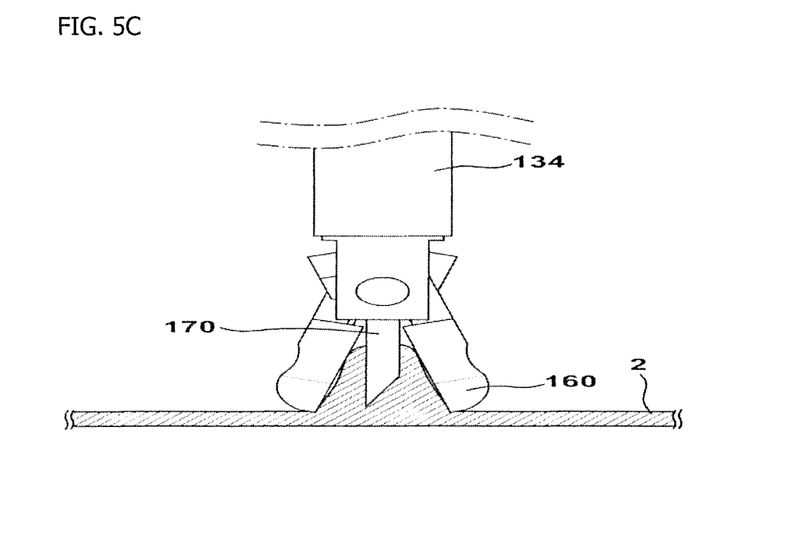

Further illustrates the operation state of the endoscopic injection apparatus with the afore-mentioned features which also refers to FIG. 5A to FIG. 5C.

In order to inject an injection solution in the wall 2 which forms an outer surface of the tissue which is the patient's injection targeted area, first move the endoscopic injection apparatus 100 closer to the patient's body tissue as shown in FIG. 5A. Herein, the holding forceps 160 is spread as shown in the drawing. Further, the needle 170 is positioned inside the holding forceps 160. Herein, the needle operation button 130 does not operate. Further, even when the needle operation button 130 operates, the needle 170 does not slide. In other words, the spread angle of the holding forceps 160 is spread above the predetermined angle.

The operator moves the endoscopic injection apparatus 100 further closer to the wall 2 which forms the outer side of the tissue thereby, a part of the wall 2 may be held between the holding forceps 160 which is practically spread.

In this state, the operator pulls the forceps operation unit 120 backwards i.e., in the direction which the needle operation button 130 is formed to hold a part of the wall 2 which is the injection targeted area. Then the holding forceps 160 closes by the pulling of the first wire which is connected to the forceps operation unit 120 and holds a part of the wall 2 as shown in FIG. 5B. Herein, the holding forceps 160 is completely closed or may be slightly spread. This is because when the holding forceps 160 is holding the wall 2 thick, it may not maintain spreading angle as much as the above thickness. Further, the holding forceps 160 may spread corresponding to the thickness of the wall 2. However, although the holding forceps 160 is slightly spread, the needle 170 is inserted to the desirable position since the holding forceps is pulling a part of the wall 2.

Herein, the sensor is configured to sense the spread angle of the holding forceps 160 and provides the result through the notification unit. Accordingly, when the notification unit such as the lamp is on, the spread angle of the holding forceps 160 spreads above the predetermined angle. Thereby, the operator knows that the needle operation button 130 is not operable. Likewise, if the holding forceps 160 is spread enough that the needle operation button 130 may not be operable, the operator may have to repeat operating the forceps operation unit 120.

When the holding forceps 160 holds the wall 2, the operator operates the needle operation button 130. Then, when the needle operation button 130 is operated, the needle 170 which is accommodated between the holding forceps 160 moves towards the direction of the wall 2 in a predetermined distance, and the end of the needle is inserted in the wall 2.

The above state is shown in FIG. 5C. Thereby, the needle 170 can be stably inserted in the wall 2. Herein, a method for inserting the needle 170 in the wall 2 can be applied in various forms. For example, when the needle operation button 130 is operated one time, the needle 170 may move forward in a predetermined distance. In this case, the needle 170 may not be inserted enough in the wall 2, hence, the needle operation button 130 may be operated many times.

Referring to FIG. 5C, when the needle 170 is completely inserted in the wall 2 as the operator operates the needle operation button 130, another operator injects an injection solution through the injection solution hole 112. Thereby, the injection solution which is provided through the injection solution hole 112 is injected in the wall through the needle 170.

Through the above process, the injection solution may be injected by accurately inserting the needle 170 in the position to be injected.

Hereinafter, when the injection of the injection solution is completed, the operator spreads the holding forceps 160 by pushing the forceps operation unit 120 towards the opposite direction which is in the direction of the shaft 134. Further, the operator moves the endoscopic injection apparatus 100 thereby, retracts the needle 170 from the wall 2. When the operator retracts the needle 170 from the wall 2, the needle 170 can be retracted by operating the needle operation button 130.

Through this process, the holding forceps 160 can hold a part of the wall 2 which forms the exterior surface of the tissue as shown in the drawing according to the exemplary embodiment of the present description, and in this state, the injection solution can be injected through the needle 170. Likewise, since the holding forceps 160 holds the part of the wall 2, it has an effect of further expanding the area which the needle 170 is inserted. Accordingly, the injection solution may be stably injected in a state which the wall 2 is not perforated.

Meanwhile, according to an exemplary embodiment of the present description, in case bleeding occurs during operation, stanching of the bleeding area is possible without the use of a separate hemostat. In other words, when the operator confirms the bleeding, the operator puts the holding forceps 160 to surround the bleeding area. In this state, the operator pulls the forceps operation unit 120 and thereby the holding surface 164 of the holding forceps 160 is contacted with the bleeding area.

Then the operator operates the power button 124. Next, power supply is provided through the power line which is connected with the endoscopic injection apparatus 100, and the provided power is transmitted to the conductive material 164A of the holding forceps 160 through the second wire. Consequently, the bleeding area may be stanched by the heat which is transmitted to the holding forceps 160.

BEST MODE FOR CARRYING OUT THE INVENTION

Figure 6:
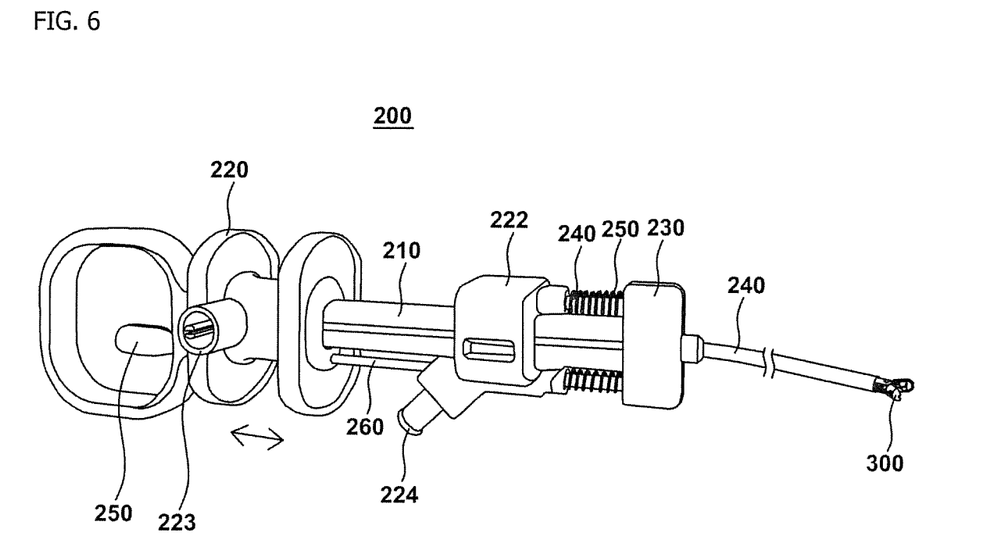
FIG. 6 is a perspective view of an endoscopic injection apparatus according to another exemplary embodiment of the present description.

FIG. 6 is a perspective view of an endoscopic injection apparatus according to another exemplary embodiment of the present description.

The endoscopic injection apparatus according to another exemplary embodiment of the present description has a similar feature with that of the afore-mentioned endoscopic injection apparatus. However, there are differences in the feature which the forceps operation unit configured to operate the holding forceps to move backwards by a spring in a state of moving forward, and the feature of avoiding interference between the wires which are respectively operated by the needle and forceps hence, hereinafter illustrates the differences of the features.

As shown in FIG. 6, the body 210 which forms the frame of the endoscopic injection apparatus 200 is included.

The body 210 includes a forceps operation unit 220 and an auxiliary operation unit 222 which slides with the forceps operation unit 220. Herein, a power connection unit 223 is formed on the forceps operation unit 220 and the injection solution hole 224 is formed on the auxiliary operation unit 222. Further, the auxiliary operation unit 224 is connected with the fixing unit 230 which is fixed on an end of the body 210 through a guide 240. A spring 250 which is an elastic member is installed on the guide 240. The spring 250 is compressed and relaxed according to forward and backward operation of the tong operation unit 220. Through this, the holding forceps (310, 320, FIG. 9) is spread or closed. That is, when the forceps operation unit 220 moves forward, the spring 250 is compressed and the holding forceps 310, 320 are spread at a predetermined angle and hereinafter, when a finger leaves from the forceps operation unit 220, the forceps operation unit 220 moves backwards due to the restoration force of the spring 250 and thereby, the holding forceps 310, 320 are closed. The holding forceps 310, 320 are operated by the holding forceps operation wire (not shown) which operates as linked with the forceps operation unit 220. The holding forceps operation wire is connected with the holding forceps 310, 320 through a shaft 240. Herein, the shaft 240 includes a power wire (not shown) configured to apply heat for stanching and an after-mentioned needle operation wire (not shown). The power wire is connected with the power connecting unit 223.

A needle operation button 250 configured to move the needle is formed on one end of a body 210. Herein, in a cross section view of the body 210, the needle operation button 250 is not formed in the middle of the body but leaning towards one side of the body 210. It is shown leaning downwards in the diagram. Further, a wire storage guide 260 is transversely connected with the needle operation button 250. The needle operation wire (not shown) is provided in the wire storage guide 260, and the needle operation wire is connected with the needle through the wire storage guide 260 and the shaft 240.

This is to operate without interference between the needle operation wire and the holding forceps operation wire.

Meanwhile, the needle according to the present description extends outside through an end of the shaft 240 and the part of the extended needle is positioned between the holding forceps 310, 320 of the holding unit 300.

However, the needle in the shaft 240 may be formed thinner than the inside diameter of the shaft 240 so that the needle may move inside the shaft 240. In this case, although there is a guide groove in the holding forceps 310, 320, there may be a problem that the needle may not be accurately inserted in the position where the injection solution may be provided since the needle moves inside the shaft 240. Thus, in order to prevent this, a fixing member 400 can be installed configured to further stably fix the needle on a part of an end of the shaft 240.

Figure 7:
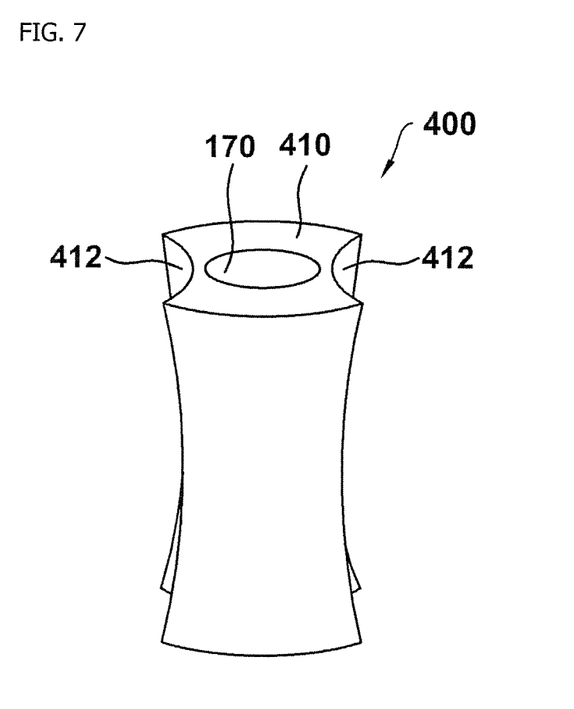
FIG. 7 is a diagram of a fixing member which is applied on exemplary embodiment of the present description.

The feature of fixing member 400 is illustrated in FIG. 7.

Referring to FIG. 7, the fixing member 400 is formed with a body of a predetermined length and diameter to be inserted and installed in the shaft 240.

Further, the opposite side units 412 of the fixing member 400 body 410 is formed in a concave shape. This is to fixate the needle 170 which is in the middle.

Figure 8:
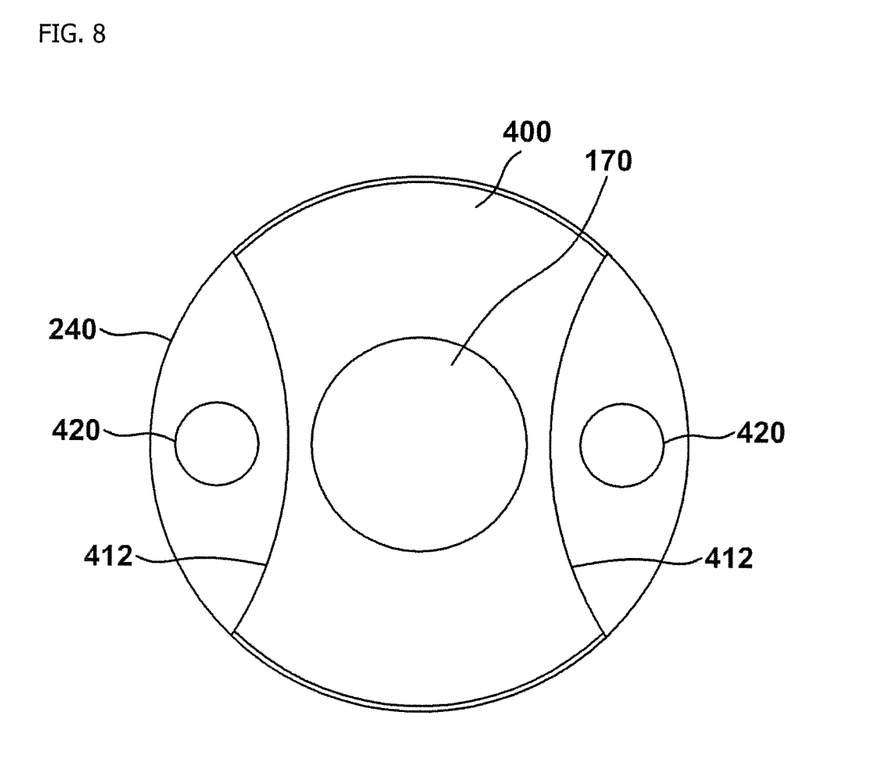
FIG. 8 is an end view illustrating a fixing member of FIG. 7 installed on a shaft.

In other words, referring to FIG. 8 illustrating the fixing member 400 installed in the shaft 240, it prevents the needle 170 from severely shaking inside the shaft 240 since the side units 412 of the concave fixing member 400 is formed close with the needle 170. This refers that the needle 170 may stably slide that much. Herein the side unit 412 of the fixing member 400 has a concave shape, thereby a predetermined space is formed between the side unit 412 of the fixing member 400 and an inner side of the shaft 240. The holding forceps operation wire 420 is formed on the predetermined space. The holding forceps operation wire 420 is respectively connected to the holding forceps 310, 320.

The fixing member 400 can be formed in a different form. In other words, referring to FIG. 8, the left and right side units 412 have a concave shape however, other parts may also have a concave shape. Further, it is also possible that left, right, top and bottom parts can all have a concave shape. That is, if it has a feature which may somewhat fixate the needle, it is not limited to a certain shape.

Figure 9:
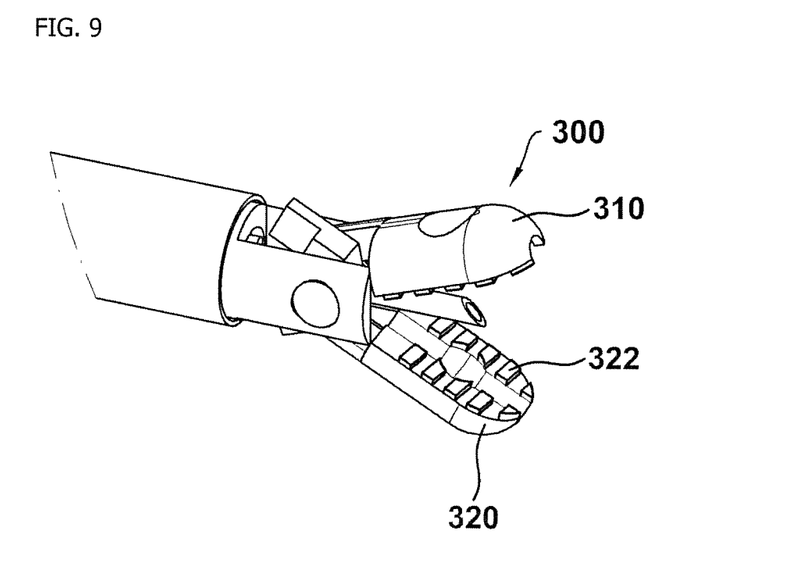
FIG. 9 is an exemplary diagram illustrating a holding surface of a holding forceps according to an exemplary embodiment of the present description.

FIG. 9 is an exemplary diagram illustrating a holding surface of a holding forceps according to an exemplary embodiment of the present description.

Referring to FIG. 9, a holding surface 322 of a holding forceps 310, 320 have a concavo-convex shape. When they are formed in a concavo-convex shape, a feature of holding the injection targeted area tissue is expected to further improve. When the holding feature is improved, the needle may be further accurately inserted in the wall.

Herein, the holding surface 322 is configured to stanch the bleeding area as afore-mentioned and for this, the holding surface is formed with a conductive material. The range of the holding surface 322 which is formed with a conductive material may be a part or the whole holding surface 322.

As afore-mentioned, according to an exemplary embodiment of the present application, after first holding the body tissue to be injected using the holding forceps, stably insert the needle in the body tissue and inject the injection solution and, enable stanching of the bleeding area.

While this invention has been described in connection with what is presently considered to be practical exemplary embodiments, it is to be understood that the invention is not limited to the disclosed embodiments, but, on the contrary, is intended to cover various modifications and equivalent arrangements included within the spirit and scope of the appended claims. Accordingly, the scope of the present disclosure shall be determined only according to the attached claims.

That is, the exemplary embodiment of the present application is characterized by holding the tissue using the holding forceps through forceps operation unit, and then operating the needle operation button and inserting the needle in the tissue, and hereinafter the injection solution is injected through the injection solution hole, however the slide of the needle and the injection process of the injection solution can be operated with one touch operation.

INDUSTRIAL APPLICABILITY

The present application may be applied when injecting medicine in the patient's body during endoscopic surgery or medical examination. Further, the present application can be applied on various medical fields such as the field of endoscope which use endoscopic apparatus for stanching of the bleeding area.

What is claimed is:
1. An endoscopic injection apparatus comprising:
a needle configured to eject an injection solution;
a pair of holding forceps which surrounds the needle;
an operation unit configured to hold an injection targeted area using the pair of holding forceps and injects the injection solution when the needle is inserted in a tissue;
a sensor configured to sense a spread angle of the pair of holding forceps; and
a notification unit configured to display a sensing result of the sensor,
wherein the operation unit comprises:
a body with a needle operation button on one end;
an injection hole for the injection solution which is formed on the body; and
a forceps operation unit configured to operate the pair of holding forceps according to a sliding movement and surround a body exterior,
wherein the needle operation button is configured to operate only when the spread angle of the pair of holding forceps is within a predetermined angle, wherein the predetermined angle is selected to be a state in which the pair of holding forceps are holding the injection targeted area,
wherein the endoscopic injection apparatus further comprises:
a predetermined length of a shaft which is connected with another end of the body and wherein a fixing piece is formed within an inner one end of the shaft and a part of the fixing piece protrudes outside the shaft and the pair of holding forceps is installed in hinged to the fixing piece with an incision unit formed in the middle of the fixing piece; and
a fixing member configured to fix the needle which is formed with a predetermined length and diameter as to be inserted and installed in the shaft,
wherein the fixing member has at least one side that is formed in a concave shape in a needle direction and a predetermined space is formed between the at least one side of the fixing member and an inner side of the shaft.

2. The endoscopic injection apparatus of claim 1, further comprising a power button configured to control a power supply which is applied from a power supply unit to the pair of holding forceps.

3. The endoscopic injection apparatus of claim 2, wherein the power button operates only when the needle operation button is not operating.

4. The endoscopic injection apparatus of claim 1, wherein a guide groove is formed on a holding surface of the pair of holding forceps for the movement of the needle.

5. The endoscopic injection apparatus of claim 4, wherein a conductor configured to generate heat by a power supply which is transmitted according to the control of a power button and is formed on an end of the holding surface.

6. The endoscopic injection apparatus of claim 1, wherein while the needle operation button is operated, the needle moves as much as a predetermined distance and the needle is inserted in the tissue.

7. The endoscopic injection apparatus of claim 1, wherein the body further comprises an elastic member configured for a forward and backward movement of the forceps operation unit.

\* \* \* \* \*